(12) United States Patent
Tkachuk et al.

(10) Patent No.: US 8,692,997 B2
(45) Date of Patent: Apr. 8, 2014

(54) OPTICAL GAS AND/OR PARTICULATE SENSORS

(75) Inventors: Michael Tkachuk, Sayville, NY (US); Michael Gouzman, Centereach, NY (US)

(73) Assignee: BAH Holdings LLC, Glen Cove, NY (US)

( * ) Notice: Subject to any disclaimer, the term of this patent is extended or adjusted under 35 U.S.C. 154(b) by 373 days.

(21) Appl. No.: 13/217,179

(22) Filed: Aug. 24, 2011

(65) Prior Publication Data

US 2012/0057161 A1     Mar. 8, 2012

Related U.S. Application Data

(60) Provisional application No. 61/376,974, filed on Aug. 25, 2010.

(51) Int. Cl.
*G01N 21/00* (2006.01)

(52) U.S. Cl.
USPC ............................................. 356/437; 356/439

(58) Field of Classification Search
USPC ........................................ 356/432, 437–439
See application file for complete search history.

(56) References Cited

U.S. PATENT DOCUMENTS

| | | | |
|---|---|---|---|
| 3,329,005 | A | 7/1967 | Levy et al. |
| 4,736,103 | A | 4/1988 | Nelson et al. |
| 4,885,469 | A | 12/1989 | Yamagishi et al. |
| 5,602,647 | A | 2/1997 | Xu et al. |
| 5,696,586 | A | 12/1997 | Ivanov |
| 5,886,348 | A | 3/1999 | Lessure et al. |
| 6,147,351 | A | 11/2000 | Huiku |
| 6,342,948 | B1 | 1/2002 | Gilby |
| 6,369,387 | B1 * | 4/2002 | Eckles .......................... 250/343 |

(Continued)

FOREIGN PATENT DOCUMENTS

| | | |
|---|---|---|
| EP | 0 359 213 | 9/1989 |
| EP | 0 396 319 | 3/1996 |

(Continued)

OTHER PUBLICATIONS

Search Report mailed Jul. 27, 2001 for PCT Application PCTGB0100711.

(Continued)

*Primary Examiner* — Tara S Pajoohi Gomez

(74) *Attorney, Agent, or Firm* — James P. Muraff; Neal, Gerber & Eisenberg LLP

(57) ABSTRACT

A gas or particulate sensor is provided for the detection of at least two target gases and/or particulates. The sensor comprises: a chamber for containing a gas sample under test; a first optical measurement channel configured for the detection of a first target gas or particulate within the gas sample, and a second optical measurement channel configured for the detection of a second target gas or particulate within the gas sample, each optical measurement channel comprising a respective optopair which comprises a radiation source adapted to emit radiation and a radiation detector adapted to output a signal in response to detected radiation; and focusing optics able to form an image of an object. At least the first optical measurement channel is configured such that the radiation detector of the respective optopair receives via the focusing optics an image of the corresponding radiation source, whereby the radiation received from the radiation source by the radiation detector is modified by the first target gas or particulate present in the gas sample such that the output signal from the radiation detector provides information as to the presence of the first target gas or particulate in the gas sample.

18 Claims, 7 Drawing Sheets

(56) References Cited

U.S. PATENT DOCUMENTS

| | | |
|---|---|---|
| 6,956,648 B2 | 10/2005 | Loicht et al. |
| 7,063,667 B1 | 6/2006 | Ben-Oren et al. |
| 7,570,360 B1 | 8/2009 | Tkachuk |
| 7,796,265 B2 | 9/2010 | Tkachuk |
| 2002/0063216 A1 | 5/2002 | Clausen et al. |
| 2003/0090670 A1 | 5/2003 | Capetanopoulos |
| 2008/0079942 A1 | 4/2008 | Buettner et al. |
| 2009/0235720 A1 | 9/2009 | Smith |
| 2009/0257064 A1 | 10/2009 | Tkachuk |
| 2009/0268204 A1 | 10/2009 | Tkachuk |
| 2011/0116079 A1 | 5/2011 | Tkachuk |

FOREIGN PATENT DOCUMENTS

| | | |
|---|---|---|
| EP | 1987346 B1 | 8/2010 |
| EP | 1922532 B1 | 12/2012 |
| JP | 62261032 A | 11/1987 |
| JP | 01049937 B | 10/1989 |
| WO | 0140748 A1 | 6/2001 |
| WO | 0165219 A1 | 9/2001 |

OTHER PUBLICATIONS

Search Report mailed May 3, 2001 for PCT Application PCTGB0004523.

Search Report mailed Nov. 25, 2009 for Great Britain Application No. GB0919794.8.

Unpublished co-pending U.S. Appl. No. 13/426,494, filed Mar. 21, 2012 (which is not being furnished herewith, pursuant to the Commissioner's Notice dated Sep. 21, 2004).

* cited by examiner

OPTICAL GAS AND/OR PARTICULATE SENSORS

CROSS-REFERENCE TO RELATED PATENT APPLICATIONS

This application is a non-provisional application which claims priority to U.S. Patent Application No. 61/376,974, filed on Aug. 25, 2010, which is incorporated herein by reference in its entirety.

FIELD OF THE INVENTION

This invention relates to optical sensors for detecting multiple gases and/or particulates.

BACKGROUND

Many critical safety and environmental applications require monitoring not only of one gas concentration, but of several gases. For example, the air control equipment in mines has to control the methane concentration and also the concentration of oxygen, and it is therefore necessary to monitor both the concentration of methane and that of oxygen in the mine atmosphere. Conventional equipment comprises a set of the required sensors, usually different types for different gases (e.g. catalytic for methane, electrochemical for oxygen, etc). The recent major tendency in the gas analysis industry is a transition towards optical sensors since these are generally believed to be the most accurate and reliable. The most developed optical technology for gas analysis is nondispersive infrared (NDIR) technology, but at present this cannot be utilized for the whole range of gases required by industry (for instance, there is no NDIR sensor for oxygen). Nevertheless, other optical technologies could be used to cover the shortage for the multi-gas optical sensors.

SUMMARY OF THE INVENTION

We have invented novel methods for simultaneously detecting, in one unit, the presence of multiple gases and/or particulates (e.g. smoke) using optical techniques. In the following document we will explain this method and its implementation for lenses and mirror-based setups. The optical detection methods can be used for multiple gases and also gas mixtures.

Our method utilizes the same physical volume and main optical components for different types of measurements which can be made at the same time (i.e. concurrently). In such a way we can provide a more compact and less expensive detection system.

In accordance with a first aspect of the present invention, a gas or particulate sensor for the detection of at least two target gases and/or particulates is provided, comprising:
 a chamber for containing a gas sample under test;
 a first optical measurement channel configured for the detection of a first target gas or particulate within the gas sample, and a second optical measurement channel configured for the detection of a second target gas or particulate within the gas sample, each optical measurement channel comprising a respective optopair which comprises a radiation source adapted to emit radiation and a radiation detector adapted to output a signal in response to detected radiation; and
 focusing optics able to form an image of an object;
wherein at least the first optical measurement channel is configured such that the radiation detector of the respective optopair receives via the focusing optics an image of the corresponding radiation source, whereby the radiation received from the radiation source by the radiation detector is modified by the first target gas or particulate present in the gas sample such that the output signal from the radiation detector provides information as to the presence of the first target gas or particulate in the gas sample.

The disclosed technique makes it possible to share the same volume of a gas chamber at the same time for multiple measurements of different or similar nature (e.g. absorbing, fluorescent, line spectrum analysis, scattering, etc.), so that two or more gases or particulates can be detected concurrently. This is achieved by using focusing optics to form an image of each optopair's radiation source (which, at least in the first optical measurement channel, is received by the corresponding detector), thereby constraining the light channel to a particular location within the sensor. In this way, any one gas measurement can be spatially localized, taking place independently and without affecting any other measurement made simultaneously within the chamber. In some examples, two or more of the optopairs may share a radiation source or detector: thus it is not essential that a dedicated radiation source and detector must be provided for each channel.

Each respective measurement channel can operate on the same or different optical measurement principles, e.g. NDIR, fluorescent probe or scattering (each described below), and can be adapted for the detection of different target gases through selection of each operating wavelength/fluorescent probe material, etc. as appropriate to the measurement principle of that channel.

Depending on the measurement principle to be utilized on the second measurement channel, the respective optopair may or may not be configured in the same way as described above. In a preferred embodiment, the second optical measurement channel is configured such that the radiation detector of the respective optopair receives via the focusing optics an image of the corresponding radiation source, whereby the radiation received from the radiation source by the radiation detector is modified by the second target gas or particulate present in the gas sample such that the output signal from the radiation detector provides information as to the presence of the second target gas or particulate in the gas sample. In this case, it will be appreciated that the images of the radiation sources of the two optopairs will be at different locations.

Hence the optopairs can be arranged to implement the same or different detection mechanisms. In general, at least one of the optopairs may operate according to the NDIR technique. Therefore, preferably, at least one of the optopairs is adapted to operate at a wavelength which is absorbed by the target gas and/or scattered by the target particulate, whereby a reduction in the radiation intensity detected by the radiation detector is indicative of the presence of the target gas and/or particulate in the gas sample. For example, one optopair "channel" could be dedicated to monitor each target gas in question, e.g. methane and CO. The wavelength of each channel would be set accordingly by selecting a wavelength known to be absorbed by the target gas in question. This could be achieved by choosing the wavelength at which the source emits, or that to which the detector is responsive and/or by inserting an optical filter into the light path. It should be noted that this arrangement can also be used to detect the presence of particulates such as smoke, since the received intensity will be reduced by scattering of the radiation.

In a particularly preferred embodiment, the first optical measurement channel is adapted to operate on the NDIR principle, the respective optopair operating at a first wavelength known to be absorbed by the first target gas or particulate.

In further preferred embodiments, the second optical measurement channel may also or alternatively be adapted to operate on the NDIR principle, the respective optopair operating at a second wavelength known to be absorbed by the second target gas or particulate.

Other detection mechanisms may be appropriate, e.g. for the monitoring of gases such as oxygen for which the NDIR technique does not work. A particularly preferred example involves the addition of a "fluorescent probe" to the optopair, the emission characteristics of which are affected by the presence of the target gas. Therefore, preferably, at least one of the optopairs further comprises a gas sensitive component located within the chamber on the radiation path between the radiation source and the radiation detector, the gas sensitive component comprising a fluorescent or luminescent material adapted to emit radiation in response to incident radiation from the radiation source, the fluorescent or luminescent response of the material being dependent on the presence of a target gas or particulate in the gas sample, wherein the radiation detector is adapted to detect radiation emitted by the gas sensitive component.

Thus, in another preferred embodiment, the first optical measurement channel comprises a respective optopair which includes a gas sensitive component disposed in a radiation path between the radiation source and the radiation detector, the gas sensitive component comprising a fluorescent or luminescent material adapted to emit radiation in response to incident radiation from the radiation source, the fluorescent or luminescent response of the material being dependent on the presence of the first target gas or particulate in the gas sample.

In further preferred embodiments, the second optical measurement channel may also or alternatively comprise a respective optopair which includes a gas sensitive component disposed in a radiation path between the radiation source and the radiation detector, the gas sensitive component comprising a fluorescent or luminescent material adapted to emit radiation in response to incident radiation from the radiation source, the fluorescent or luminescent response of the material being dependent on the presence of the second target gas or particulate in the gas sample.

Using this "fluorescent probe" mechanism, the measurements can be disrupted if the detector receives radiation directly from the light source or ambient light. As such, preferably, the at least one of the optopairs further comprises one or more optical filters configured to reduce the amount of radiation other than that emitted by the gas sensitive component reaching the radiation detector.

In a particularly preferred embodiment, the second optical measurement channel is configured such that the radiation detector of the respective optopair does not receive an image of any radiation source, whereby any radiation received by the radiation detector from any radiation source is scattered by the second target gas or particulate present in the gas sample such that the output signal from the radiation detector provides information as to the presence of the second target gas or particulate in the gas sample, the second target gas or particulate preferably being smoke. This is particularly sensitive particulate-detection technique. In this embodiment in particular it may be desirable to share one radiation source between the first and second measurement channels, with one detector completing the first optopair located at the image of the radiation source, and a second detector completing the second optopair located away from the image of the radiation source.

Whatever the mechanism on which the measurement channel operates, the effects of ambient light can be further reduced if the intensity of the radiation emitted by the radiation source of at least one of the optopairs is modulated. The modulated signal can be extracted from the output of the detector and used to deduce the presence or concentration of the target gas without influence from ambient light.

Any combination of the above optical detection methodologies—or other appropriate techniques—can be incorporated into a multi-gas/particulate sensor through configuration of each opto-pair.

The focusing optics could take any form capable of forming an image within a defined focal plane. In a particularly preferred embodiment, the focusing optics comprise a spherical or elliptical mirror, the first and second focal planes being one and the same focal plane. In other examples, the focusing optics comprise a lens system, preferably a convex lens, disposed between the first and second focal planes. The same optical component (e.g. mirror or lens) preferably provides focusing for all of the opto-pairs included in the sensor.

In accordance with another aspect of the invention, a gas or particulate sensor for the detection of at least two target gases and/or particulates is provided, comprising:
  a chamber for containing a gas sample under test;
  first and second optopairs, each comprising a radiation source adapted to emit radiation and a radiation detector adapted to output a signal in response to detected radiation; and
  focusing optics able to form an image of an object located in a first focal plane at a second focal plane;
wherein, for each optopair, the respective radiation source is disposed substantially in the first or second focal plane of the focusing optics to thereby form an image of the radiation source in the other of the first and second focal planes of the focusing optics, and the respective radiation detector is disposed substantially in the other of the first and second focal planes of the focusing optics at the location of the image of the radiation source to thereby receive the image of the respective radiation source, the radiation path between the respective radiation source and the respective radiation detector passing through the chamber, whereby the radiation received from the respective radiation source by the respective radiation detector is modified by a target gas or particulate present in the gas sample such that the output signal from the radiation detector of the first optopair provides information as to the presence of a first target gas and/or particulate, and the output signal from the radiation detector of the second optopair provides information as to the presence of a second target gas and/or particulate.

In particularly preferred implementations, the sensor further comprises a scattered radiation detector disposed away from the location(s) of the image(s) of the radiation source(s) of the optopair(s), at least one of the radiation source(s) being adapted to emit radiation at a wavelength which is scattered by a target particulate, whereby the presence of the target particulate in the gas sample causes radiation to be scattered away from the image of the radiation emitter, to be received by the scattered radiation detector.

It should be noted that, depending on the type of focusing optics used, the first and second focal planes may in practice be one and the same. For instance, in certain preferred implementations, the focusing optics comprise a spherical or elliptical mirror, the first and second focal planes being one and the same focal plane.

In other preferred examples, the focusing optics comprise a lens system, preferably a convex lens, disposed between the first and second focal planes.

In accordance with another aspect of the invention, a particulate sensor for the detection of at least one target particulate is provided, comprising:
a chamber for containing a gas sample under test;
an optopair comprising a radiation source adapted to emit radiation and a radiation detector adapted to output a signal in response to detected radiation; and
focusing optics able to form an image of an object located in a first focal plane at a second focal plane;
wherein the radiation source is disposed substantially in the first focal plane of the focusing optics to thereby form an image of the radiation source in the second focal plane of the focusing optics, and the radiation detector is disposed at a position away from the location of the image of the radiation source, whereby in the absence of the target particulate in the gas sample, the radiation detector receives substantially no radiation from the radiation source, the detection of radiation by the radiation detector being indicative of scattering by the target particulate present in the gas sample.

BRIEF DESCRIPTION OF THE DRAWINGS

Examples of gas and/or particulate sensors in accordance with the invention will now be described and contrasted with conventional sensors, with reference to the accompanying drawings, in which.

DETAILED DESCRIPTION OF PREFERRED EMBODIMENTS

Figure 1:
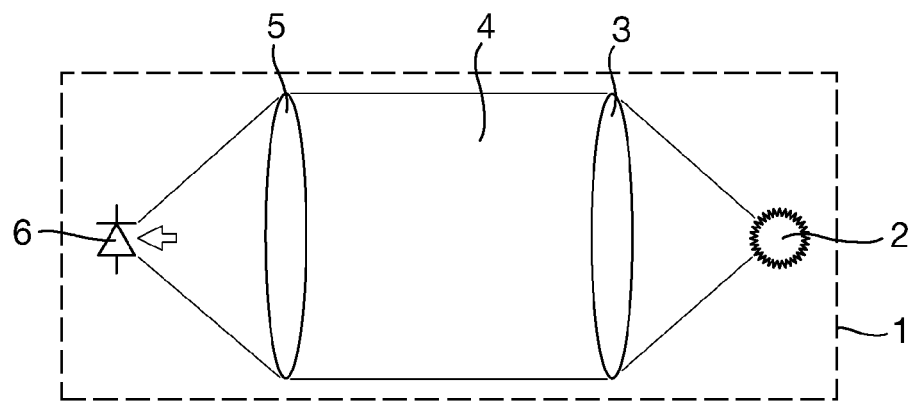
FIG. 1 shows an example of a conventional NDIR sensor.

Throughout the Figures, like components are represented with the same reference numeral.

A conventional NDIR technique of gas detection in a chamber is presented in FIG. 1, which depicts an optical gas sensor with a linear, lens-based optic structure. This can be implemented in a minimal configuration using a gas filled chamber 1 in combination with a narrow optical band light source 2, a collimation lens 3, a focusing lens 5 and a photoelectrical converter (photodetector) 6. The parallel light beam 4 crosses the most part of the gas chamber 1. In such implementations the absorption in the selected optical band represents the concentration of a preselected gas of interest which is known to absorb in that optical waveband.

Figure 2:
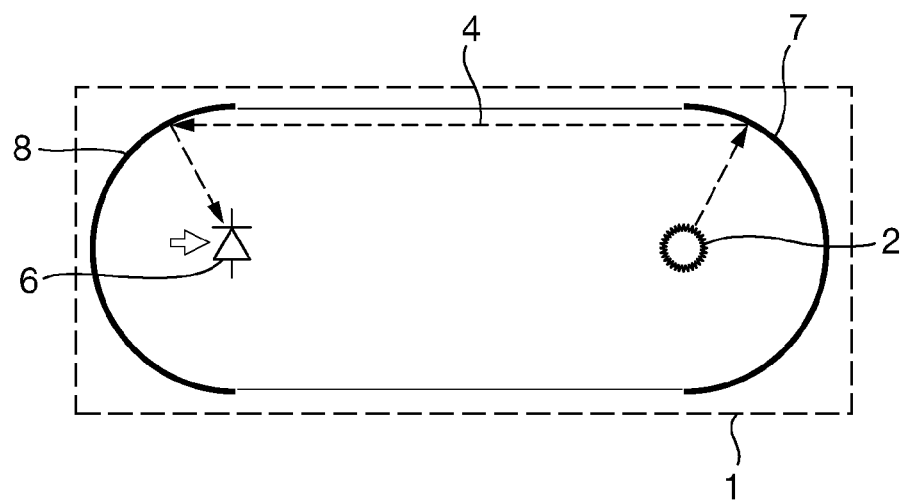
FIG. 2 shows another example of a conventional NDIR sensor.

Another implementation of a direct absorption detection technique is presented in FIG. 2. Here, the lenses have been replaced by spherical mirrors 7 and 8, which increases the active volume inside the gas chamber 1 and eliminates wavelength limitation. Such limitation is caused by the optical properties of lenses 3 and 5 in the FIG. 1 example.

Figure 3:
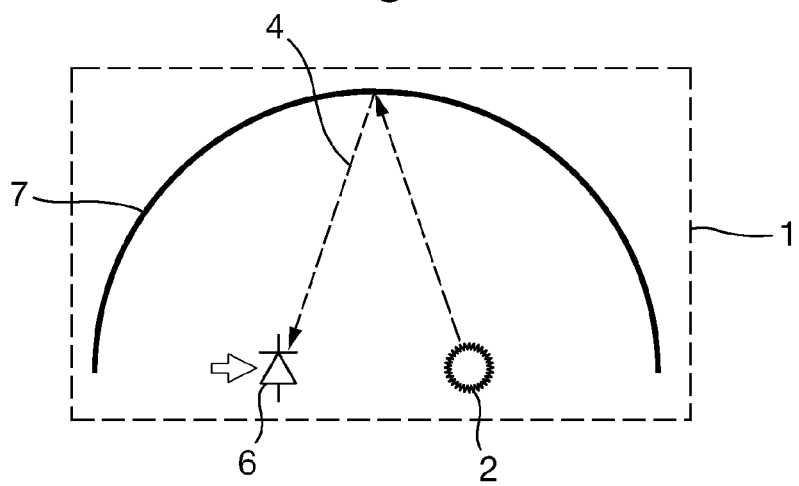
FIG. 3 shows a further example of a NDIR sensor.

One more design of a gas sensor is presented in FIG. 3. This design is based on the ability of a spherical mirror to project an image of an object in a focal plane. An image of a light source 2 will be projected onto a photoelectrical converter 6 if both of the components (2 and 6) are:
in the focal plane;
at the same distance as each other from the focus center;
arranged on the same diameter (i.e. on a straight line which intersects the focus center).

Figure 4:
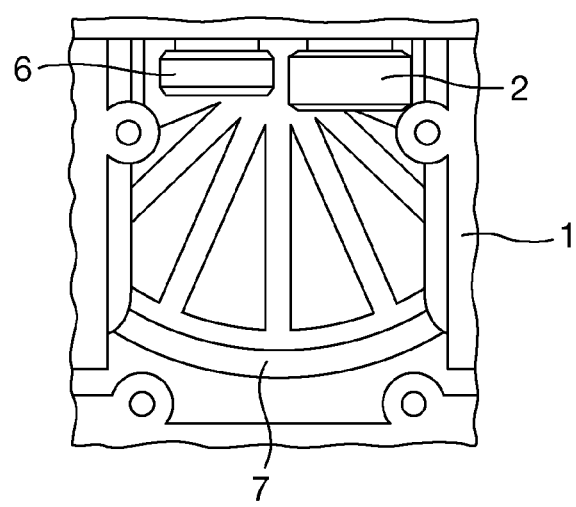
FIG. 4 is a photograph showing a practical implementation of a sensor configured as shown in FIG. 3.

FIG. 4 is a photograph showing selected components of such a gas sensor. The presented sensor uses known absorption properties of the selected gas. Light source 2 and photoelectrical converter 6 have to be selected for specific optical wavelength. Each gas or group of gases can be detected by detecting absorption on such a selected wavelength.

The general limitation of all of the detectors (sensors) presented above is caused by nature of the detection method—the single selected wavelength and light path do not enable the detection of two or more gases and it is not possible to make use of different physical or physical-chemical effects in the same gas chamber 1 with the same optical element 7.

Multi-Gas Optical Sensor

In preferred embodiments, we propose to use a spherical mirror and to utilize the effect of geometrical symmetry for multiplying the number of opto-pairs (each having a light source 2 and photoelectrical converter 6, though in some cases one or other of the components can be shared by more than one opto-pair) with different working wavelengths or physical-chemical properties and different target gases or other objects. Alternatively, a lens system can be used in place of the mirror.

Figure 5:
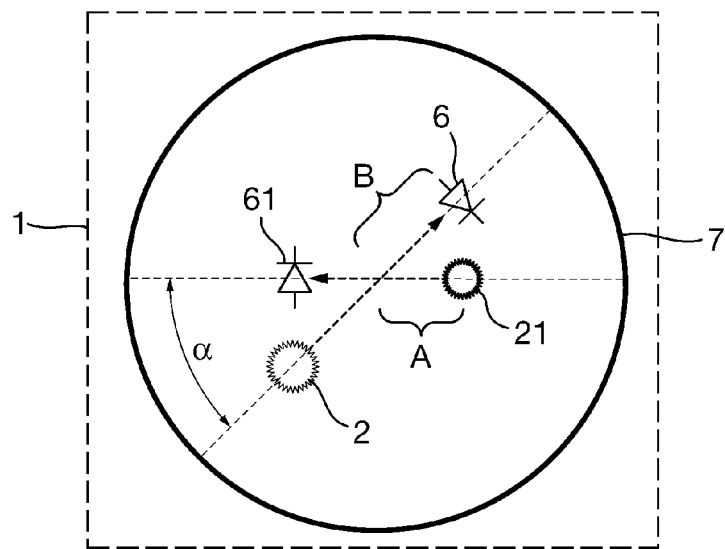
FIG. 5 schematically shows components of a first embodiment of a gas sensor in accordance with the invention.

A plan view of a first embodiment of such a sensor is shown in FIG. 5. Inside the gas chamber 1 is installed a spherical mirror 7. Two opto-pairs are disposed in the focal plane of the spherical mirror 7. Each opto-pair is installed along one diameter (i.e. along a straight line intersecting the central axis of the mirror 7). The configuration, is such that an independent signal can be obtained from each opto-pair, such that each opto-pair acts as an individual measurement "channel", albeit making use of the same physical space within the chamber volume. To make it possible we have to provide the two opto-pairs with a difference at least in one of four parameters, namely:
physical-chemical mechanism of detection;
distance from the center (radii "A" and "B" in FIG. 5);
angle between selected diameters ("α" in FIG. 5);
an operational wavelength.

For some detection configurations we can use more than one photoelectrical converter (photodetector) in optical communication with the same light source. Similarly, more than one light source could be arranged to deliver light to a single photodetector.

Some possible implementations of the proposed method will now be discussed for different types of optical sensor configuration.

Detecting Concentration of Two or More Gases by Measurement of Absorption on Specific Wavelengths This implementation will be discussed with reference to FIG. 5. Two light sources 2 and 21 are installed at different distances ("A" and "B") from the focal point (the center of the depicted circle representing mirror 7). Light beams from both light sources travel in accordance with the laws of geometrical optics and focus on photoelectrical converters 6 and 61. The first opto-pair, made up of light source 2 and detector 6, operates at a first selected wavelength $\lambda_1$, and the second opto-pair, made up of light source 21 and detector 61, operates at a second selected wavelength $\lambda_2$, where $\lambda_1$ is different from $\lambda_2$. For the two selected wavelengths $\lambda_1$ and $\lambda_2$, the corresponding coefficients of absorption can be measured. Then it is possible to calculate the concentration of both gases by using a calibration table.

Both light sources 2 and 21 as well as photoelectrical converters 6 and 61 can be installed along the same diameter or on two different diameters with non-zero angle α between them. One application for such a dual scheme would be the simultaneous measurement of concentration for a selected gas (e.g. CO, a combustion gases, etc.) and water vapor (which is considered to be a "gas" for the purposes of this disclosure).

Figure 6A:
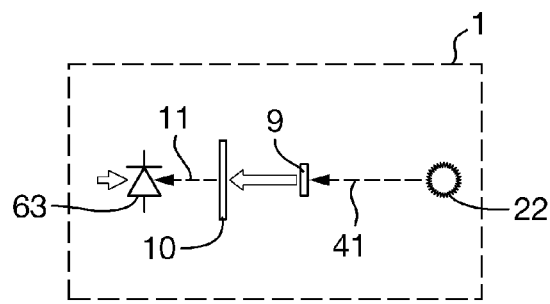
FIG. 6a schematically shows components of a second embodiment of a gas sensor in accordance with the invention.

Detecting Concentration of a Gas by Measurement of Luminescent Parameters of Fluorescent Probes Another type of the optical sensor compatible for use with the same multi-channel optical scheme is based on the known effect of fluorescent quenching in presence of specific gases (e.g. oxygen, carbon monoxide, etc.). One possible configuration is presented in FIG. 6a. In the presented implementation, light source 22 produces an excitation light beam 41. A gas sensitive substance 9 (which can be referred to as a "fluorescent probe") is arranged in the light path between the light source 22 and a detector 63. The substance is specifically sensitive to the target gas (e.g. oxygen) in the sense that its light emission characteristics are dependent on the concentration of that target gas to which the material is exposed. One example of a suitable gas sensitive substance is 1-decyl-4-(1-pyrenyl) butanoate, the emission spectra of which is significantly quenched in the presence of oxygen. The substance can be provided as a coating on a substrate, for example.

Figure 6B:
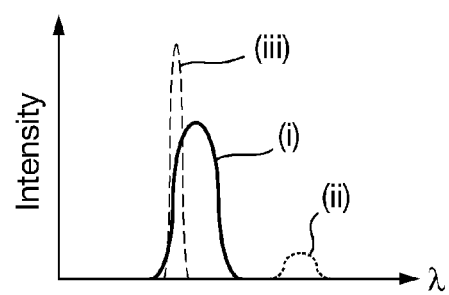
FIG. 6b illustrates relevant radiation spectra.

The narrow short wavelength optical spectrum of light source 22 should overlap with at least part of the excitation spectrum of gas sensitive substance 9. This is illustrated in FIG. 6(b), where trace (i) represents the excitation spectra of the gas-sensitive substance 9, and trace (ii) its emission spectra, either or both of which may vary depending on the local concentration of target gas. Trace (iii) depicts the radiation waveband emitted by radiation source 22 and it will be seen that this overlaps the excitation spectra (ii). It may be necessary to install a band-pass or step optical filter 10 to minimize the amount of excitation light in the emission spectrum of the beam 11 reaching the detector 63.

Three different implementations of this detection method will be discussed now:
1. Fluorescent probe and optical filter integrated with photoelectrical converter (detector).
2. Fluorescent probe and optical filter integrated with light source.
3. Fluorescent probe and optical filter integrated with light source plus second optical filter integrated with photoelectrical converter.

Figure 7:
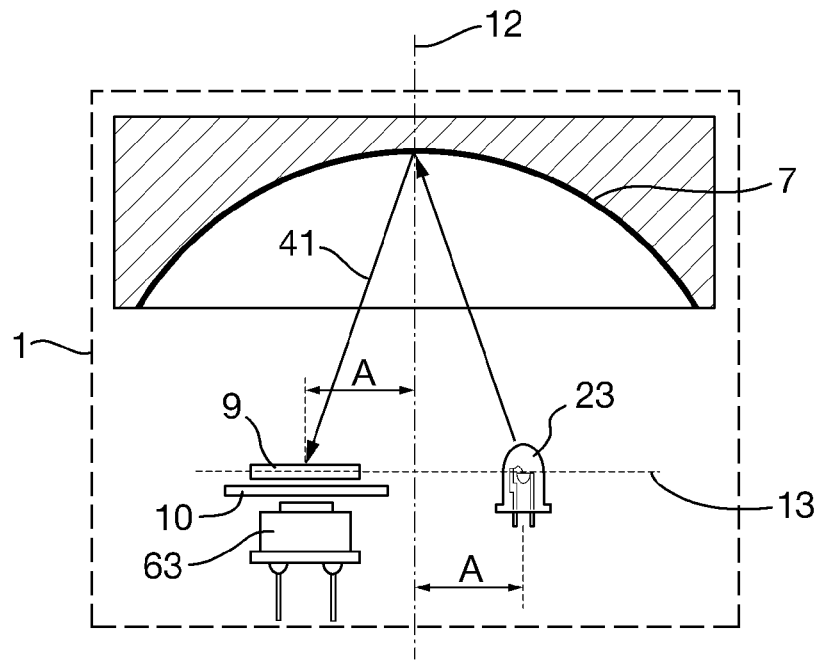
FIGS. 7 to 9 show three further embodiments of gas sensors in accordance with the invention.

An embodiment of a gas sensor with a fluorescent probe and an optical filter integrated with the photoelectrical converter (detector) is presented in FIG. 7. Inside the gas chamber 1, a spherical mirror 7 (here presented as a cross section) is installed. Spherical mirror 7 has an optical principal axis 12 (axis of the geometrical symmetry). At equal distances "A" from the optical principal axis 12, a light source 23 (e.g. an LED) and a photoelectrical converter 63 (e.g. a Light-to-Voltage Converter such as a photo diode) are installed. Light source 23 is installed in such a way, that the effective center of its light emission is in the focal plane 13 of the spherical mirror 7. An excitation light beam 41 is emitted by light source 23 and then reflected and concentrated by the spherical mirror 7, finally illuminating gas sensitive substance 9. The gas sensitive substance 9 is positioned at the same distance "A" and on the same diameter as that on which light source 23 is installed. Such installation can guarantee delivery maximum of optical energy from light source 23 to gas sensitive substance 9. A wavelength-selective optical filter 10 is installed between gas sensitive substance 9 and photoelectrical converter 63. The filter 10 reduces so-called "dark current" of the photoelectrical converter 63 by reducing any portion of incoming light (the excitation light beam 41 is emitted by light source 23 and ambient light) which has not been absorbed by gas sensitive substance 9. The output signal of photoelectrical converter 63 is a voltage (or current). This voltage can be converted to give the concentration of the selected gas according to a calibration table.

Figure 8:
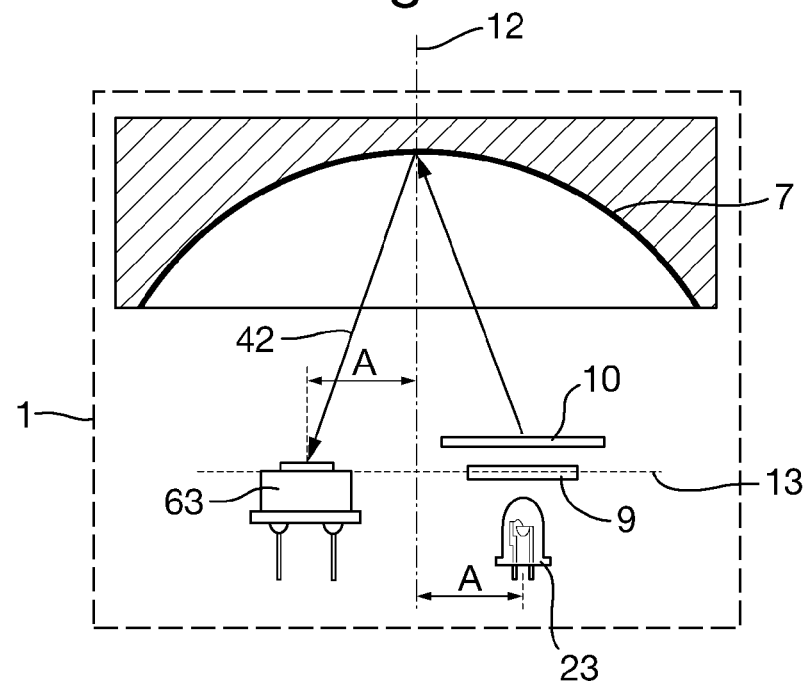

FIG. 8. represents an embodiment of a gas sensor with a fluorescent probe and an optical filter integrated with the light source 23. In the given configuration light source 23 is installed below focal plane 13. The gas sensitive substance 9 is installed in the focal plane 13 and illuminated directly by light source 23. Optical filter 10 covers the gas sensitive substance 9. Such configuration (directly illuminated gas sensitive substance 9 in focal plane 13 and distance "A" between the optical principal axis 12 and center of the gas sensitive substance 9) produces an optical beam 42 of emission wavelengths from gas sensitive substance 9. An image of the emitting zone of the gas sensitive substance 9 is projected by the optical beam 42 onto the photoelectrical converter 63. For better sensitivity, the photoelectrical converter 63 should be positioned on the focal plane 13 at distance "A" from the optical principal axis 12. The presented configuration can eliminate illumination of gas sensitive substance 9 by ambient light, but cannot protect the photoelectrical converter 63 from randomly incoming ambient light. Modulation of the intensity of the light source 23 can reduce the inaccuracy in measurement associated with randomly incoming ambient light.

Figure 9:
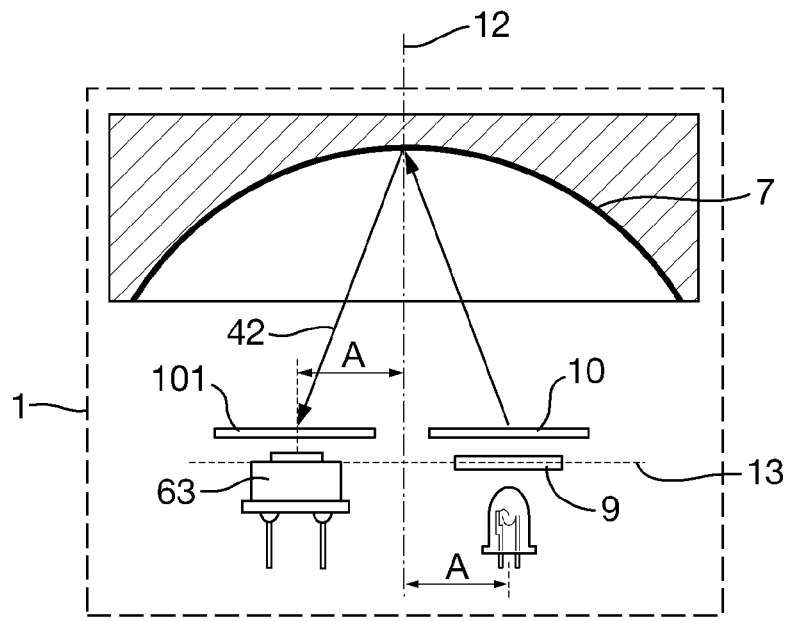

In the embodiment of FIG. 9, a fluorescent probe is integrated with the light source, and two filters are installed. This is believed to provide the highest level of protection from ambient light—here, the gas sensitive substance 9 is protected by filter 10, and additional protection for the photoelectrical converter 63 is provided by additional filter 101. The FIG. 9 embodiment can also use light source modulation for further protection from ambient light generated signals.

Implementation of the said method presented in FIG. 7 produces the biggest response from the detector (per watt of energy expended in illuminating the gas sensitive substance 9), and hence the best signal to noise ratio. However, the FIG. 9 embodiment is less sensitive to ambient light. If the detector receives additional light from ambient sources (or elsewhere), this produces an additional background shift of the signal output by the photodetector, which makes the range of possible output signals more narrow. In other words, the dynamic range (the ratio of the maximal possible signal from the detector to the signal equivalent to the noise level) is reduced. Thus, the FIG. 9 implementation gives the best dynamic range of the signal from photoelectrical converter 63

One or more measurement channels operating on the above described fluorescent probe principle can be incorporated into a multi-gas sensor by appropriate configuration of selected opto-pairs. For example, in the scheme shown in FIG. 5, one or both of the opto-pairs shown (i.e. opto-pair 2, 6 and/or opto-pair 21,61) could be configured as shown in any of FIGS. 7 to 9, by introducing an appropriate gas sensitive component. For instance, in one embodiment, a NDIR channel as described above with reference to FIG. 5 could be provided using opto-pair 2, 6 configured at an appropriate wavelength for the detection of methane, and the second opto-pair 21,61 could be configured to include a fluorescent probe so as to detect oxygen. Any number of channels operating on either principle could be included.

Detecting the Presence of Micro Particles (Particulates) in Gas Chamber (e.g. Smoke Detector)

Figure 10:
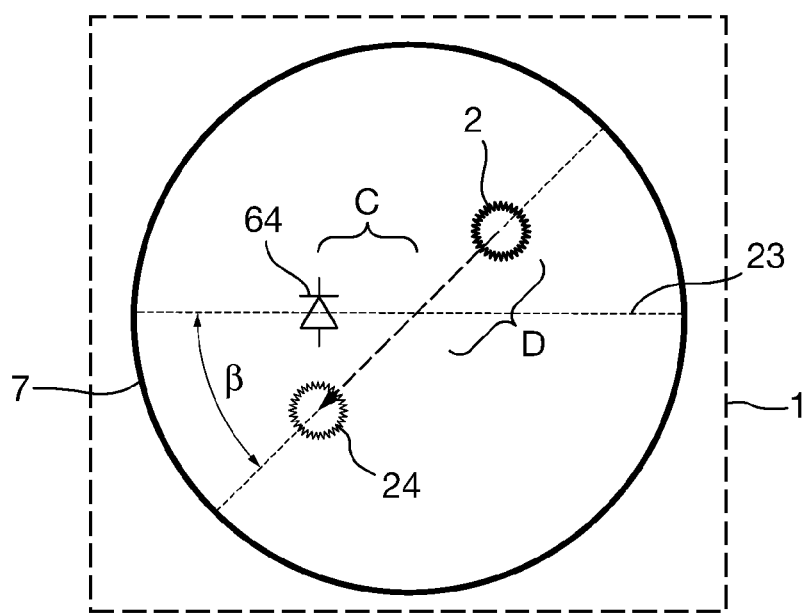
FIGS. 10 to 14 schematically show components of more embodiments of gas sensors in accordance with the invention.

An optical micro particle detector can be designed based on the general multi-gas detection structure discussed above, and an example of the principle on which this may operate is shown in FIG. 10.

Light source 2 is installed at a distance "D" from the center of the spherical mirror 7. The image of the light source 2 is projected onto a point 24 at an equal distance "D" from the centre on the same diameter as the light source, according to the rules of geometrical optics.

In contrast with gas detection configurations (e.g. as shown in FIG. 3 and FIG. 5), here the photoelectrical converter 64 is not installed at point 24. Instead, its position has to be characterized by having a different distance "C" (where C≠D) from the center of the spherical mirror 7, or by being located on a different diameter, with an angle β between the two diameters (where β≠0), or by the presence of both of these conditions (C≠D and β≠0).

In the presented configuration, photoelectrical converter 64 will register only scattered light. In the absence of particulates within the chamber (e.g. smoke or steam), the light beam output by the light source 2 will be focused at point 24 and will not illuminate the photodetector. Thus the receipt of light at the photodetector is indicative of the presence of particulates within the chamber. The intensity of scattered light received at the photodetector is a function of small particle concentration in the gas chamber 1.

A particle detector such as this can be incorporated into a multi-substance detector by combining the arrangement of FIG. 10 with one or more measurement channels operating on any of the principles described above with reference to FIGS. 5 to 9. For example, an opto-pair operating on the NDIR principle (FIG. 5) might be provided, configured for the detection of CO, alongside a particulate detection channel operating on the FIG. 10 principle. The opto-pair for particulate detection could take the form of a second light source and a second detector. Alternatively, the channel could share the same light source as the NDIR channel, such that only a second detector need be provided. The detector should be arranged at a position where no image of a light source (of any of the opto-pairs) is formed, such that it will only receive scattered light.

Simultaneous Use any of the Above Possible Methods in the Same Chamber

Figure 11:
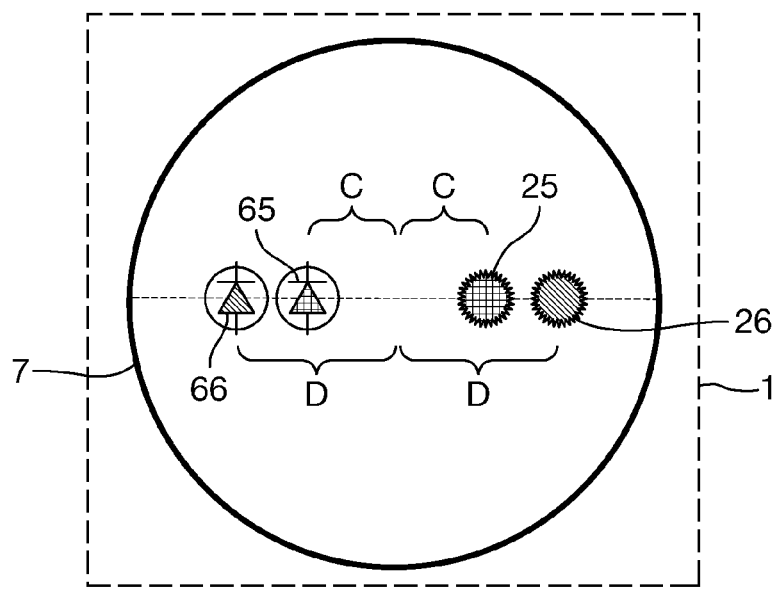

FIG. 11 shows a multi-gas detection system according to a further embodiment with a plurality of light sources 25, 26 and a plurality of photoelectrical converters 65, 66. In this example, the light sources and the detectors are all arranged along the same diameter, but at different distances "C" and "D" from the center of spherical mirror 7.

Some of the measurement channels implemented by the opto-pairs may operate on the NDIR principle at wavelengths selected to correspond to those absorbed by the target gas(es), whilst others may include a fluorescent probe as described above, responsive to another selected gas.

The number of such "opto-pairs" (in this case the first opto-pair is formed of components 25 and 65, and the second of components 26 and 66) is limited only by diameter of the spherical mirror 7 and corresponding size parameters of the light sources and photoelectrical converters. The efficiency of the "opto-pairs" is higher closer to the center of the sensor. Some (or all) of the light sources and photoelectrical converters can be used as part of the optical micro particle detector implementation, described above, e.g. by providing a detector which is not positioned to receive an image of one of the light sources.

Figure 12:
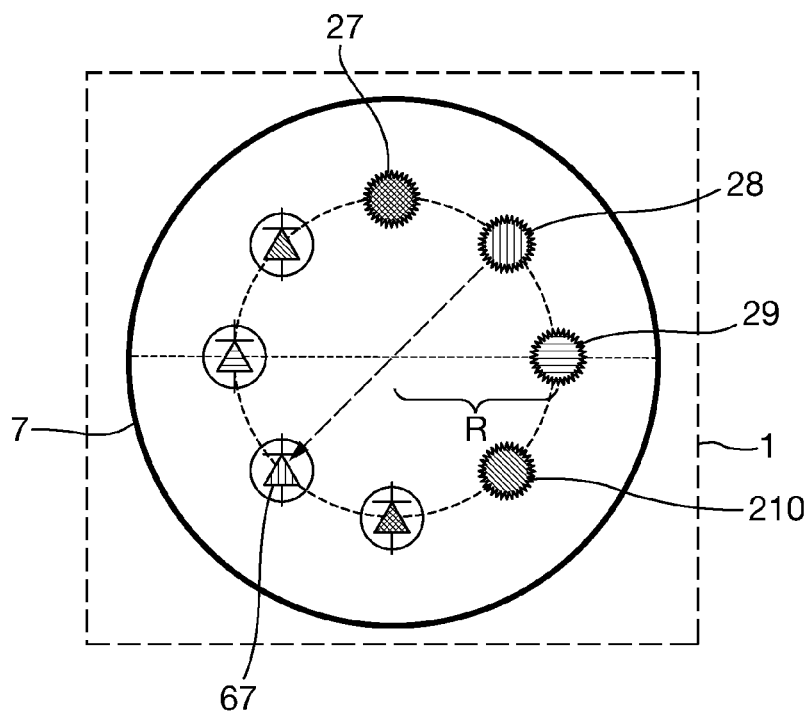

Another exemplary implementation is presented in FIG. 12. In this implementation of the proposed method, all of the light sources 27, 28, 29, and 210 are located at the same distance from the center of the spherical mirror 7. The light sources and photoelectrical converters are arranged in a circle with radius "R". Each "opto-pair" is aligned along a diameter of the sensor (as an example, "opto-pair" 28-67 is arranged on the diameter indicated by a bold, broken line). In the presented implementation, all of the "opto-pairs" are at an equal position from the centre of the sensor and hence have equal energetic efficiency. Some (or all) of light sources and photoelectrical converters can be used as part of the optical micro particle detector implementation described above, e.g. by providing a detector which is not positioned to receive an image of one of the light sources. The number of such "opto-pairs" (28 and 67, etc.) that can be deployed is limited only by the radius "R" of the spherical mirror 2 and corresponding size parameters of the light sources and photoelectrical converters.

Figure 13:
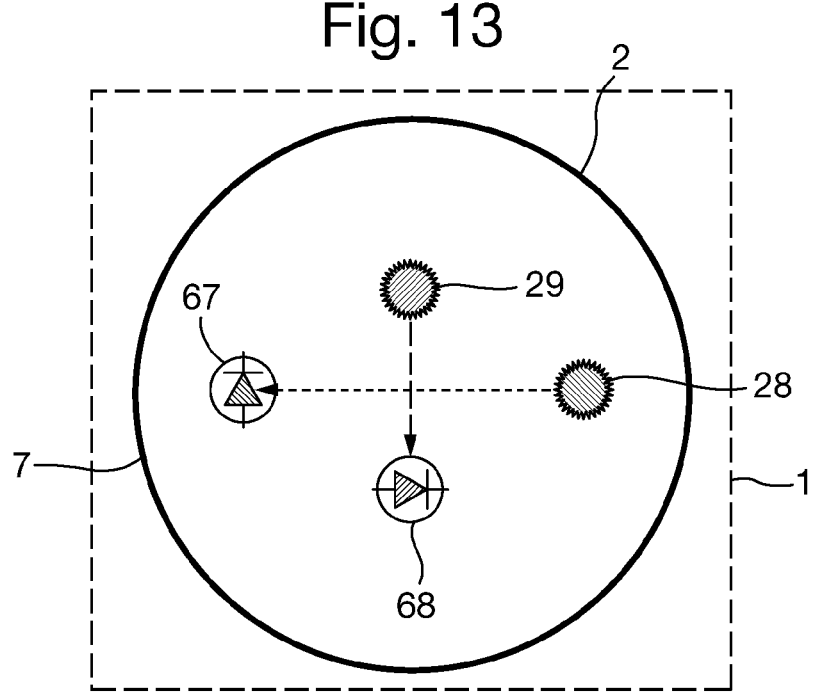

FIG. 13 represents a more general implementation of the proposed method. Each of the "opto-pairs" is situation along its own diameter and at a selected distance from the center. The number of said "opto-pairs" can be increased or multiplied by installing more components along the same diameter(s) (but with different distance from the centre) or at the same distance from the centre (but along additional diameters).

Some (or all) light sources and photoelectrical converters in the implementation can be used as part of the optical micro particle detector implementation described above, e.g. by providing a detector which is not positioned to receive an image of one of the light sources. The number of such "opto-pairs" (28 and 67, etc.) is limited only by the sectional area of the spherical mirror 2 and the sectional areas of light sources and photoelectrical converters.

If included, the small particles photodetector could be placed in the center of the mirror and it could use any (or all) of the light source(s) for the monitoring of the scattering light from the presence of the small particles (e.g. smoke) in the chamber.

All of the presented embodiments are described as using a spherical mirror but could be implemented alternatively with other focusing optics able to form an image of the or each light source. For example, the spherical mirror could be replaced by elliptical mirrors or lenses.

Figure 14:
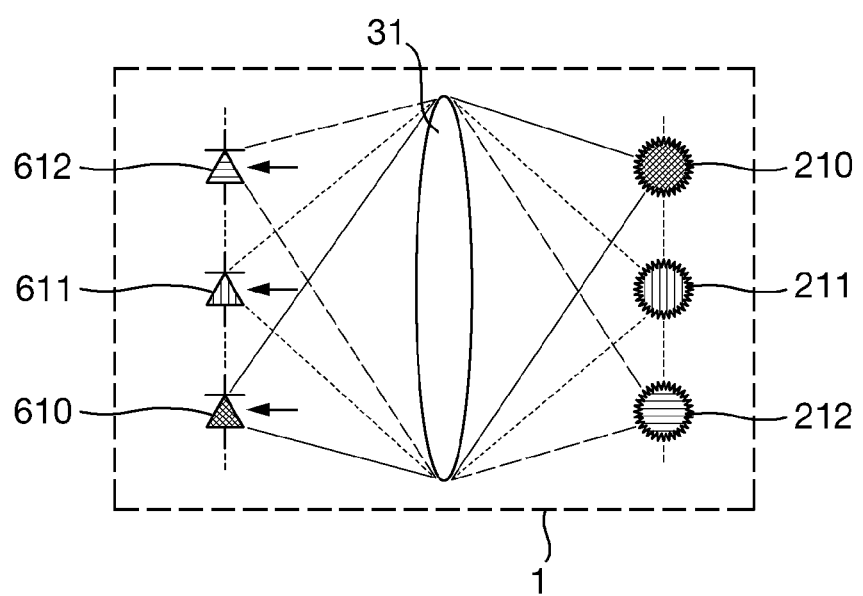

As an example, FIG. 14 presents a multi-gas optical sensor utilising a single lens 31 in place of the spherical mirror of previous embodiments. In this configuration, each of the "opto-pair" is split in two parts: an illumination source in a first focal plane and a photoelectrical converter in a second focal plane of the same lens 31. For example, in the implementation shown in FIG. 14, lens 31 forms an image of source 210 at the location of detector 610, an image of source 211 at the location of detector 611, and an image of source 212 at the location of detector 612. Thus source 210 and detector 610 form a first optopair, source 211 and detector 611 form a second optopair, and source 212 and detector 612 form a third optopair. Each optopair can operate at a different wavelength (by selection of the wavelength emitted by the source, selection of the wavelength to which the detector is responsive, and/or use of a filter in the light path), and hence be used to monitor a different target gas.

Alternatively or in addition, one or more of the optopairs could be used to detect changes in the parameters of a luminescent or fluorescent probe, by inserting a gas sensitive material into the light path, as described above with reference to FIGS. 6 to 9.

Further, one or more of the detectors could be used to detect scattered light from particles such as smoke, using the technique described above with reference to FIG. 10. This could be achieved by providing a detector in a position at which the lens does not form an image of any of the light sources.

The invention claimed is:

1. A gas or particulate sensor for the detection of at least two target gases and/or particulates, comprising:
   a chamber for containing a gas sample under test;
   a first optical measurement channel configured for the detection of a first target gas or particulate within the gas sample, and a second optical measurement channel configured for the detection of a second target gas or particulate within the gas sample, each optical measurement channel comprising a respective optopair which comprises a radiation source adapted to emit radiation and a radiation detector adapted to output a signal in response to detected radiation; and
   focusing optics able to form an image of an object;
   wherein at least the first optical measurement channel is configured such that the radiation detector of the respective optopair receives via the focusing optics an image of the corresponding radiation source, whereby the radiation received from the radiation source by the radiation detector is modified by the first target gas or particulate present in the gas sample such that the output signal from the radiation detector provides information as to the presence of the first target gas or particulate in the gas sample.

2. A gas or particulate sensor according to claim 1, wherein the second optical measurement channel is configured such that the radiation detector of the respective optopair receives via the focusing optics an image of the corresponding radiation source, whereby the radiation received from the radiation source by the radiation detector is modified by the second target gas or particulate present in the gas sample such that the output signal from the radiation detector provides information as to the presence of the second target gas or particulate in the gas sample.

3. A gas or particulate sensor according to claim 1, wherein at least one of the optopairs is adapted to operate at a wavelength which is absorbed by the respective target gas and/or scattered by the respective target particulate, whereby a reduction in the radiation intensity detected by the radiation detector is indicative of the presence of the respective target gas and/or particulate in the gas sample.

4. A gas or particulate sensor according to claim 1, wherein at least one of the optopairs further comprises a gas sensitive component located within the chamber on a radiation path between the radiation source and the radiation detector, the gas sensitive component comprising a fluorescent or luminescent material adapted to emit radiation in response to incident radiation from the radiation source, the fluorescent or luminescent response of the material being dependent on the presence of a target gas or particulate in the gas sample, wherein the radiation detector is adapted to detect radiation emitted by the gas sensitive component.

5. A gas or particulate sensor according to claim 4, wherein the at least one of the optopairs further comprises one or more optical filters configured to reduce the amount of radiation other than that emitted by the gas sensitive component reaching the radiation detector.

6. A gas or particulate sensor according to claim 1, wherein the first optical measurement channel is adapted to operate on the NDIR principle, the respective optopair operating at a first wavelength known to be absorbed by the first target gas or particulate.

7. A gas or particulate sensor according to claim 1, wherein the first optical measurement channel comprises a respective optopair which includes a gas sensitive component disposed in a radiation path between the radiation source and the radiation detector, the gas sensitive component comprising a fluorescent or luminescent material adapted to emit radiation in response to incident radiation from the radiation source, the fluorescent or luminescent response of the material being dependent on the presence of the first target gas or particulate in the gas sample.

8. A gas or particulate sensor according to claim 1, wherein the second optical measurement channel is adapted to operate on the NDIR principle, the respective optopair operating at a second wavelength known to be absorbed by the second target gas or particulate.

9. A gas or particulate sensor according to claim 1, wherein the second optical measurement channel comprises a respective optopair which includes a gas sensitive component disposed in a radiation path between the radiation source and the radiation detector, the gas sensitive component comprising a fluorescent or luminescent material adapted to emit radiation in response to incident radiation from the radiation source, the fluorescent or luminescent response of the material being dependent on the presence of the second target gas or particulate in the gas sample.

10. A gas or particulate sensor according to claim 1, wherein the second optical measurement channel is configured such that the radiation detector of the respective optopair does not receive an image of any radiation source, whereby any radiation received by the radiation detector from any radiation source is scattered by the second target gas or particulate present in the gas sample such that the output signal from the radiation detector provides information as to the presence of the second target gas or particulate in the gas sample, the second target gas or particulate preferably being smoke.

11. A gas or particulate sensor according to claim 1, wherein the respective optopairs of the first measurement channel and the second measurement channel share a radiation source or share a radiation detector.

12. A gas or particulate sensor according to claim 1, wherein the intensity of the radiation emitted by the radiation source of at least one of the optopairs is modulated.

13. A gas or particulate sensor according to claim 1, wherein the focusing optics comprise a spherical or elliptical mirror or a lens system, preferably a convex lens.

14. A gas or particulate sensor for the detection of at least two target gases and/or particulates, comprising:
   a chamber for containing a gas sample under test;
   first and second optopairs, each comprising a radiation source adapted to emit radiation and a radiation detector adapted to output a signal in response to detected radiation; and
   focusing optics able to form an image of an object located in a first focal plane at a second focal plane;

wherein, for each optopair, the respective radiation source is disposed substantially in the first or second focal plane of the focusing optics to thereby form an image of the radiation source in the other of the first and second focal planes of the focusing optics, and the respective radiation detector is disposed substantially in the other of the first and second focal planes of the focusing optics at the location of the image of the radiation source to thereby receive the image of the respective radiation source, the radiation path between the respective radiation source and the respective radiation detector passing through the chamber, whereby the radiation received from the respective radiation source by the respective radiation detector is modified by a target gas or particulate present in the gas sample such that the output signal from the radiation detector of the first optopair provides information as to the presence of a first target gas and/or particulate, and the output signal from the radiation detector of the second optopair provides information as to the presence of a second target gas and/or particulate.

15. A gas or particulate sensor according to claim 14, further comprising a scattered radiation detector disposed away from the locations of the images of the radiation sources of the optopairs, at least one of the radiation sources being adapted to emit radiation at a wavelength which is scattered by a target particulate, whereby the presence of the target particulate in the gas sample causes radiation to be scattered away from the image of the radiation emitter, to be received by the scattered radiation detector.

16. A gas or particulate sensor according to claim 14, wherein the focusing optics comprise a spherical or elliptical mirror, the first and second focal planes being one and the same focal plane.

17. A gas or particulate sensor according to claim 14, wherein the focusing optics comprise a lens system, preferably a convex lens, disposed between the first and second focal planes.

18. A particulate sensor for the detection of at least one target particulate, comprising:
    a chamber for containing a gas sample under test;
    an optopair comprising a radiation source adapted to emit radiation and a radiation detector adapted to output a signal in response to detected radiation; and
    focusing optics able to form an image of an object located in a first focal plane at a second focal plane;
wherein the radiation source is disposed substantially in the first focal plane of the focusing optics to thereby form an image of the radiation source in the second focal plane of the focusing optics, and the radiation detector is disposed at a position away from the location of the image of the radiation source, whereby in the absence of the target particulate in the gas sample, the radiation detector receives substantially no radiation from the radiation source, the detection of radiation by the radiation detector being indicative of scattering by the target particulate present in the gas sample.

* * * * *